United States Patent
Tanaka

(10) Patent No.: US 10,835,191 B2
(45) Date of Patent: Nov. 17, 2020

(54) X-RAY IMAGING APPARATUS

(71) Applicant: SHIMADZU CORPORATION, Kyoto (JP)

(72) Inventor: Masahiro Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/562,951

(22) Filed: Sep. 6, 2019

(65) Prior Publication Data
US 2020/0237335 A1 Jul. 30, 2020

(30) Foreign Application Priority Data

Jan. 24, 2019 (JP) .................................. 2019-010553

(51) Int. Cl.
*A61B 6/10* (2006.01)
*A61B 6/00* (2006.01)

(52) U.S. Cl.
CPC ............ *A61B 6/102* (2013.01); *A61B 6/4476* (2013.01); *A61B 6/467* (2013.01); *A61B 6/548* (2013.01); *A61B 2562/0257* (2013.01)

(58) Field of Classification Search
None
See application file for complete search history.

(56) References Cited

U.S. PATENT DOCUMENTS

| | | | |
|---|---|---|---|
| 4,987,583 A * | 1/1991 | Travanty | A61B 6/102 378/197 |
| 9,757,080 B2 * | 9/2017 | Lee | A61B 6/462 |
| 9,943,962 B2 * | 4/2018 | Sattler | A61B 6/4441 |
| 10,058,298 B2 * | 8/2018 | Lee | A61B 6/547 |
| 2014/0328456 A1 * | 11/2014 | Lee | A61B 6/547 378/28 |
| 2015/0043716 A1 * | 2/2015 | Lee | A61B 6/4452 378/98.2 |
| 2016/0193731 A1 * | 7/2016 | Sattler | B25J 19/06 606/130 |
| 2020/0237335 A1 * | 7/2020 | Tanaka | A61B 6/04 |

FOREIGN PATENT DOCUMENTS

| | | |
|---|---|---|
| JP | 2001-037753 | 2/2001 |
| JP | 2011-224120 | 11/2011 |

* cited by examiner

*Primary Examiner* — Thomas R Artman
(74) *Attorney, Agent, or Firm* — Andrew F. Young, Esq.; Nolte Lackenbach Siegel

(57) ABSTRACT

An X-ray imaging apparatus includes a drive unit configured to move an imager in a direction opposite to a side on which an obstacle is detected by a sensor when an operator causes the sensor to react while operating a permission button.

8 Claims, 6 Drawing Sheets

EMERGENCY STOP OF IMAGER DUE TO OBSTACLE DETECTION

MOVEMENT OF IMAGER USING PERMISSION BUTTON AND SENSOR

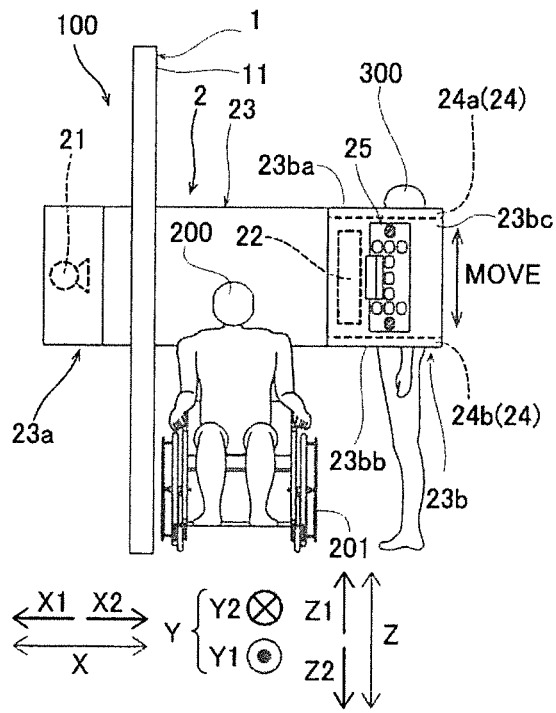
FIG.2A SECOND IMAGING STATE
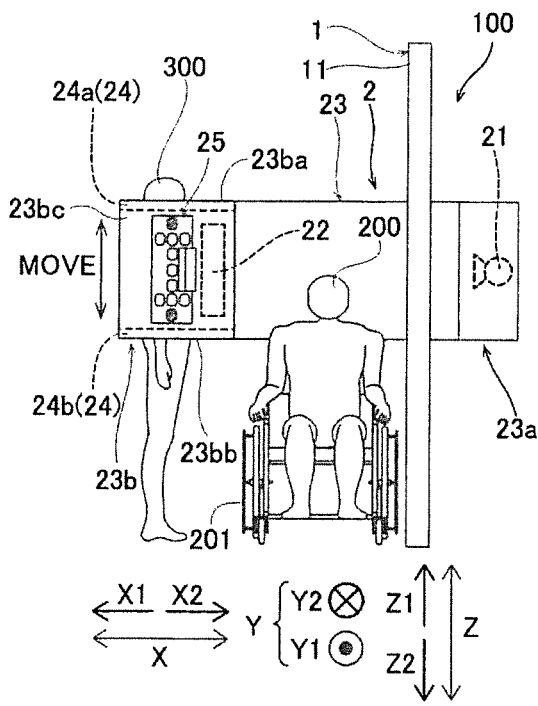
FIG.2B THIRD IMAGING STATE

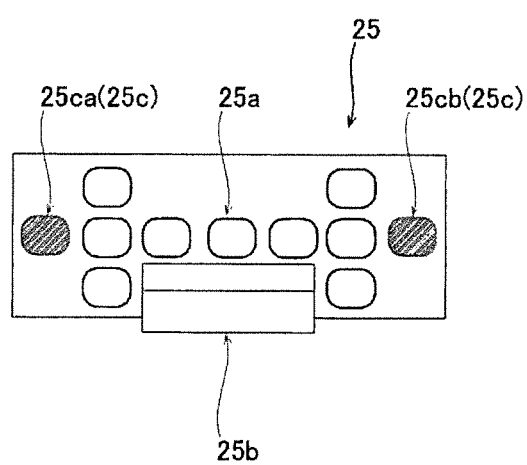

FIG.4B
EMERGENCY STOP OF IMAGER DUE TO OBSTACLE DETECTION
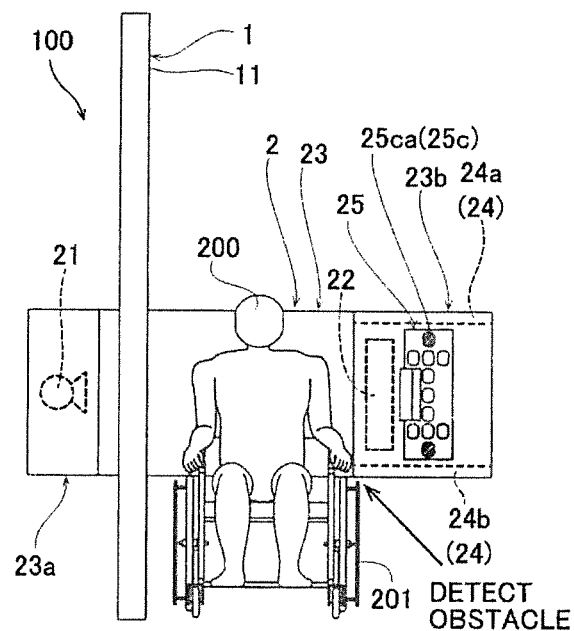
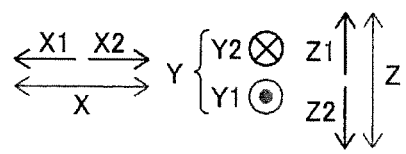

FIG.4C
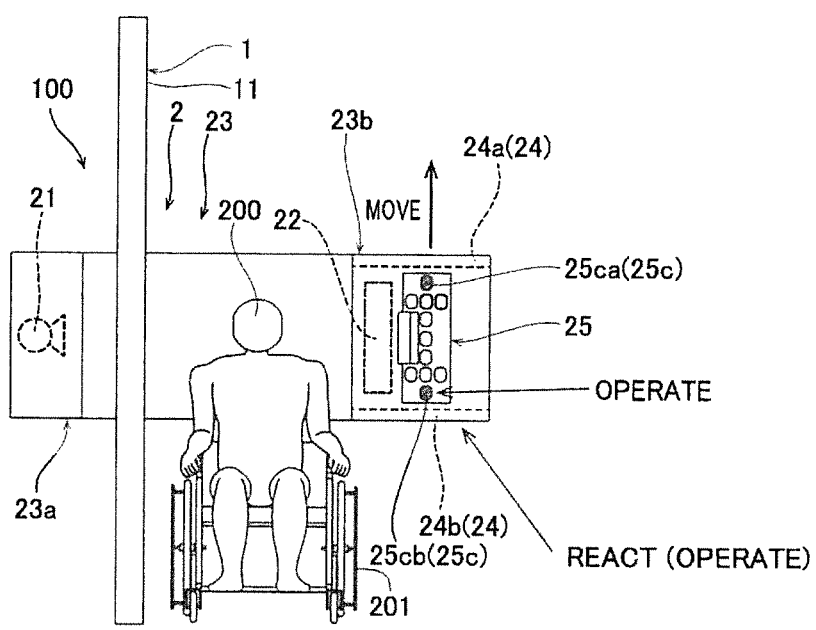
MOVEMENT OF IMAGER USING PERMISSION BUTTON AND SENSOR
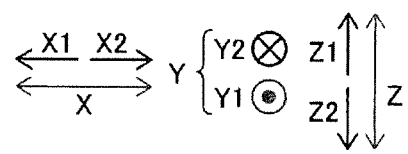

X-RAY IMAGING APPARATUS

CROSS-REFERENCE TO RELATED APPLICATIONS

This application claims the benefit of priority to Japanese Patent Application No. 2019-010553 filed on Jan. 24, 2019. The entire contents of this application are hereby incorporated herein by reference.

BACKGROUND OF THE INVENTION

Field of the Invention

The present invention relates to an X-ray imaging apparatus, and more particularly, it relates to an X-ray imaging apparatus including an imager capable of being manually moved by an operator.

Description of the Background Art

An X-ray imaging apparatus including an imager capable of being manually moved by an operator is known in general. Such an X-ray imaging apparatus is disclosed in Japanese Patent Laid-Open No. 2001-037753, for example.

Japanese Patent Laid-Open No. 2001-037753 discloses an X-ray fluoroscopic imaging table (X-ray imaging apparatus) configured to irradiate a subject placed on a table top board with X-rays from an X-ray tube. In this X-ray fluoroscopic imaging table, an operator holds a handle and applies an operating force to move an imager including the X-ray tube and an X-ray detector in the longitudinal direction and the short-side direction of the table top board. Furthermore, the X-ray fluoroscopic imaging table includes a power assist mechanism for the purpose of assisting the operator such that the operator can easily move the heavy imager.

When the operator moves the imager on the X-ray fluoroscopic imaging table described in Japanese Patent Laid-Open No. 2001-037753, it is necessary for the operator to hold the handle and receive the assistance of the power assist mechanism. However, during examination of the subject by the imager, the operator may be at a position at which the operator cannot reach the handle or at a position at which it is difficult for the operator to hold the handle. In this case, the operator needs to move to a position at which the operator can hold the handle each time in order to move the imager, and thus the time per examination disadvantageously increases.

SUMMARY OF THE INVENTION

The present invention has been proposed in order to solve the aforementioned problems, and an object of the present invention is to provide an X-ray imaging apparatus including an imager capable of being easily moved by an operator even when the operator is at a position at which the operator cannot reach a handle or at a position at which it is difficult for the operator to hold the handle.

In order to attain the aforementioned object, an X-ray imaging apparatus according to an aspect of the present invention includes a table on which a subject is placed, an imager configured to image the subject with X-rays, a drive unit configured to move the imager in a direction along a longitudinal direction of the table, a handle configured to allow an operator to manipulate movement of the imager, a sensor configured to detect an obstacle in a traveling direction of the imager when the imager is moved by the drive unit, and a permission button configured to allow the operator to permit the movement of the imager using the sensor. The drive unit is configured to move the imager in a direction opposite to a side on which the obstacle is detected by the sensor when the operator causes the sensor to react while operating the permission button.

Generally, in an X-ray imaging apparatus in which an imager can move, a sensor may be provided to detect an obstacle in the traveling direction of the imager. In this case, when the sensor detects an obstacle, the imager is urgently stopped. In the X-ray imaging apparatus according to this aspect of the present invention, easy movement of the imager by an operator is achieved by using the sensor. That is, when the imager is urgently stopped during examination of the subject, the operator can move the imager away from the obstacle using the permission button and the sensor. Consequently, even when the operator is at a position at which his or her hand cannot reach the handle or at a position at which it is difficult for the operator to hold the handle, the operator can easily move the imager away from the obstacle. Furthermore, as described above, the permission button configured to allow the operator to permit the movement of the imager using the sensor is provided such that unlike the case in which the imager is moved using only the sensor, the imager cannot be moved unless the operator intentionally operates the permission button, and thus the movement of the imager without the intention of the operator can be significantly reduced or prevented.

In the aforementioned X-ray imaging apparatus according to this aspect, the drive unit is preferably configured to move the imager while the operator causes the sensor to react while operating the permission button. According to this structure, the operator can stop the movement of the imager only by stopping the operation of the permission button or the reaction of the sensor. Consequently, the movement of the imager can be stopped easily and quickly when it is desired to stop the movement of the imager.

In the aforementioned X-ray imaging apparatus according to this aspect, the sensor preferably includes a first sensor provided on a first side in a direction of the movement of the imager by the drive unit, and a second sensor provided on a second side in the direction of the movement of the imager by the drive unit. According to this structure, both when the imager moves to the first side in the direction of movement and when the imager moves to the second side in the direction of movement, it is possible to detect an obstacle in the traveling direction of the imager and urgently stop the imager.

In this case, the drive unit is preferably configured to move the imager in an emergency stop state in a direction opposite to a side on which the obstacle is detected by the first sensor when the operator causes the first sensor to react while operating the permission button in a state in which the imager is urgently stopped due to the obstacle detected by the first sensor, and the drive unit is preferably configured to move the imager in the emergency stop state in a direction opposite to a side on which the obstacle is detected by the second sensor when the operator causes the second sensor to react while operating the permission button in a state in which the imager is urgently stopped due to the obstacle detected by the second sensor. According to this structure, both when the imager is urgently stopped due to the obstacle detected by the first sensor, and when the imager is urgently stopped due to the obstacle detected by the second sensor, the operator can move the imager away from the obstacle using the permission button and the sensor.

In the aforementioned X-ray imaging apparatus according to this aspect, the permission button preferably includes a plurality of permission buttons, and the drive unit is preferably configured to move the imager in an emergency stop state in the direction opposite to the side on which the obstacle is detected by the sensor when the operator causes the sensor to react while operating one of the plurality of permission buttons. According to this structure, the operator can move the imager using the permission button capable of being easily reached by his or her hand among the plurality of permission buttons. Consequently, it is possible to more easily manipulate the movement of the imager using the permission button and the sensor.

In this case, the plurality of permission buttons preferably include a first permission button provided on a first side in a direction of the movement of the imager by the drive unit, and a second permission button provided on a second side in the direction of the movement of the imager by the drive unit. According to this structure, the first permission button and the second permission button are provided corresponding to the direction of the movement of the imager by the drive unit, and thus even when the imager is moved to any position, it is possible to locate one of the first permission button and the second permission button at a position at which the hand of the operator can easily reach the permission button. Consequently, it is possible to still more easily manipulate the movement of the imager using the permission button and the sensor.

In the aforementioned X-ray imaging apparatus according to this aspect, the permission button is preferably provided on an operation panel provided with an operation button other than the permission button. According to this structure, the operation button and the operation button other than the permission button can be collectively provided on the operation panel, and thus the complexity of the apparatus structure can be significantly reduced or prevented as compared with the case in which the permission button is provided independently of the operation panel.

In the aforementioned X-ray imaging apparatus according to this aspect, the sensor is preferably a contact sensor configured to detect the obstacle by contact or a proximity sensor configured to detect the obstacle in a non-contact state. When the sensor is a contact sensor or a proximity sensor, an obstacle is detected at a position close to the imager, and thus the imager is urgently stopped at a position close to the obstacle. Therefore, when the sensor is a contact sensor or a proximity sensor, it is highly necessary to move the imager in an emergency stop state away from the obstacle. Thus, when the sensor is a contact sensor or a proximity sensor, with the aforementioned structure according to this aspect, the operator can immediately move the imager away from the obstacle using the permission button and the sensor even when the operator is at the position at which his or her hand cannot reach the handle or at the position at which it is difficult for the operator to hold the handle in the configuration in which it is highly necessary to move the imager in an emergency stop state away from the obstacle.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 2A is a schematic view showing a first example of the X-ray imaging apparatus in an upright imaging state according to the embodiment of the present invention.

FIG. 2B is a schematic view showing a second example of the X-ray imaging apparatus in a standing imaging state according to the embodiment of the present invention.

FIG. 3 is a schematic view illustrating an operation panel of the X-ray imaging apparatus according to the embodiment of the present invention.

FIG. 4B is a schematic view illustrating emergency stop of the imager due to obstacle detection.

FIG. 4C is a schematic view illustrating movement of the imager using a permission button and a sensor.

DESCRIPTION OF THE PREFERRED EMBODIMENTS

An embodiment of the present invention is hereinafter described with reference to the drawings.

The structure of an X-ray imaging apparatus 100 according to the embodiment of the present invention is now described with reference to FIGS. 1 to 4.

(Structure of X-Ray Imaging Apparatus)

Figure 1:
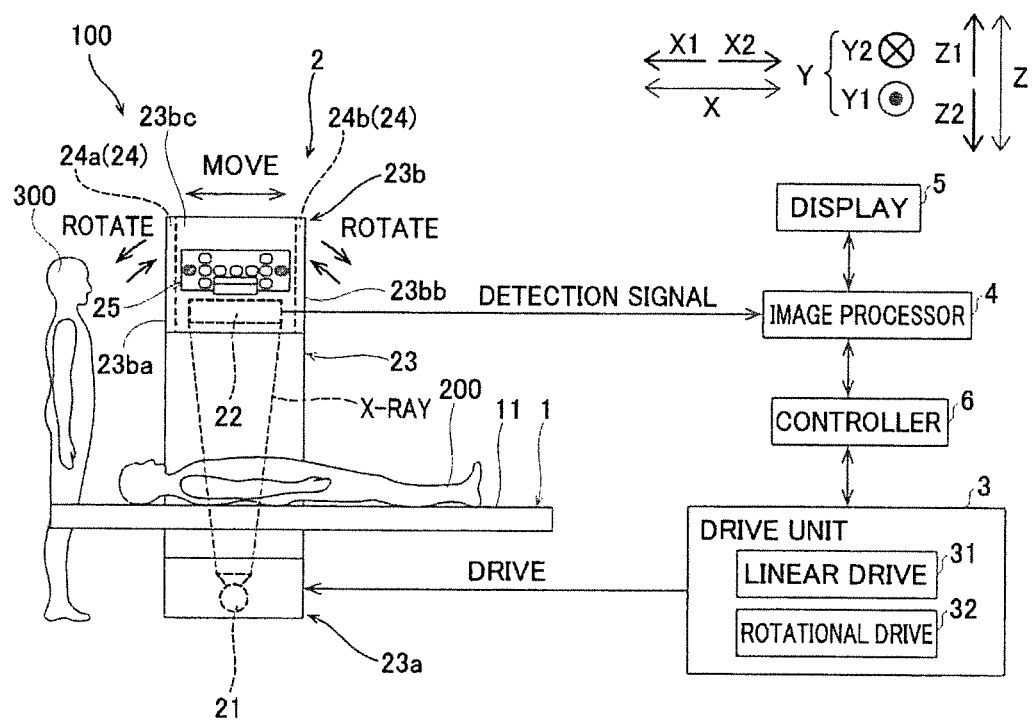
FIG. 1 is a schematic view showing the overall structure of an X-ray imaging apparatus according to an embodiment of the present invention.

As shown in FIGS. 1, 2A, and 2B, the X-ray imaging apparatus 100 is an apparatus configured to image a subject 200, which is a human, with X-rays. The X-ray imaging apparatus 100 is configured to generate an image of the inside of the subject 200 based on the results of imaging of the subject 200 with X-rays. In this embodiment, the X-ray imaging apparatus 100 is an X-ray fluoroscopic imaging apparatus (so-called X-ray television apparatus) capable of generating the image of the inside of the subject 200 in real time.

The X-ray imaging apparatus 100 includes a table 1 on which the subject 200 to be imaged (to be examined) is placed. The table 1 has a substantially rectangular shape as viewed in a direction (Z direction in FIG. 1) substantially perpendicular to a placement surface 11, which is a surface on which the subject 200 is placed. In FIG. 1, the table 1 has a longitudinal direction in an X direction and a short-side direction in a Y direction. The X-ray imaging apparatus 100 also includes an imager 2 configured to image the subject 200 with X-rays. The imager 2 includes an X-ray irradiator 21 and an X-ray detector 22. The X-ray irradiator 21 is configured to generate X-rays and irradiate the subject 200 with the X-rays. The X-ray irradiator 21 includes an X-ray tube, which is an X-ray source, and a collimator configured to adjust the irradiation range of X-rays generated by the X-ray tube, for example. The X-ray detector 22 is configured to detect the X-rays emitted from the X-ray irradiator 21 and transmitted through the subject 200. The X-ray detector 22 includes a flat panel detector (FPD), for example. The X-ray detector 22 is configured to transmit a detection signal, which is an electrical signal corresponding to the detected X-ray, to an image processor 4 described below. The structure of the imager 2 is described below in more detail.

The X-ray imaging apparatus 100 further includes a drive unit 3 configured to move the imager 2. The drive unit 3 includes a linear drive 31 and a rotational drive 32. The linear drive 31 includes a motor as a drive source, for example, and is configured to move the imager 2 in a direction (X direction in FIG. 1) along the longitudinal direction of the table 1 (straight). The rotational drive 32 includes a motor as a drive source, for example, and is configured to integrally rotate the table 1 and the imager 2 about a rotation axis that extends in the Y direction. Thus, as shown in FIGS. 1, 2A, and 2B, the rotational drive 32 is configured to change the state of the X-ray imaging apparatus 100 to a first imaging state, a second imaging state, or a third imaging state.

The first imaging state is a state in which the subject 200 is imaged in a prone position. Both the second imaging state and the third imaging state are states in which the subject 200 is imaged in an upright position or a sitting position. FIGS. 2A and 2B show examples in which the subject 200 seated on a wheelchair 201 is imaged in a sitting position. Furthermore, the second imaging state and the third imaging state are states in which the table 1 and the imager 2 in the first imaging state are rotated in rotational directions opposite to each other. In the first imaging state, the table 1 is disposed in such a manner that the placement surface 11 is parallel to a horizontal direction. Furthermore, in the second imaging state and the third imaging state, the table 1 is disposed in such a manner that the placement surface 11 is parallel to a vertical direction. In any of the first imaging state, the second imaging state, and the third imaging state, the linear drive 31 can move the imager 2 in a direction along the longitudinal direction of the table 1.

The X-ray imaging apparatus 100 further includes the image processor 4 configured to generate the image of the inside of the subject 200 based on the detection signal from the X-ray detector 22 of the imager 2. The image processor 4 includes a processor such as a GPU and a memory configured to store information, for example. The X-ray imaging apparatus 100 also includes a display 5 configured to display the image of the inside of the subject 200 generated by the image processor 4. The display 5 includes a liquid crystal monitor, for example. The X-ray imaging apparatus 100 also includes a controller 6 configured or programmed to control the operation of the X-ray imaging apparatus 100. The controller 6 includes a processor such as a CPU and a memory configured to store information.

(Detailed Structure of Imager)

The X-ray irradiator 21 and the X-ray detector 22 of the imager 2 face each other with the table 1 interposed therebetween. Specifically, the X-ray irradiator 21 is provided on the side opposite to the placement surface 11 side of the table 1 with respect to the table 1. The X-ray detector 22 is provided on the side of the placement surface 11 of the table 1 with respect to the table 1. That is, the X-ray imaging apparatus 100 is an under-tube type X-ray imaging apparatus in which the X-ray irradiator 21 is provided below the table 1.

The imager 2 includes a support 23 configured to support the X-ray irradiator 21 and the X-ray detector 22 in such a manner as to connect the X-ray irradiator 21 and the X-ray detector 22 to each other. The support 23 is provided to support the X-ray irradiator 21 by a first portion 23a, which is a first end, and to support the X-ray detector 22 by a second portion 23b, which is a second end. The first portion 23a and the second portion 23b of the support 23 face the table 1 in the direction perpendicular to the placement surface 11 of the table 1. The first portion 23a and the second portion 23b of the support 23 are respectively provided on the side opposite to the placement surface 11 of the table 1 and on the side of the placement surface 11 of the table 1 with respect to the table 1. Even when the X-ray imaging apparatus 100 is in any of the first imaging state, the second imaging state, and the third imaging state, the subject 200 is disposed between the placement surface 11 of the table 1 and the second portion 23b of the support 23.

The second portion 23b of the support 23 is provided with a sensor 24 configured to detect an obstacle in the traveling direction of the imager 2 when the linear drive 31 of the drive unit 3 moves the imager 2. In the X-ray imaging apparatus 100, when an obstacle is detected by the sensor 24, the imager 2 is urgently stopped. When the imager 2 is to be urgently stopped, the controller 6 that has acquired an obstacle detection signal from the sensor 24 may output an emergency stop command to the linear drive 31 of the drive unit 3 to urgently stop the imager 2, or the sensor 24 may directly output an obstacle detection signal as an emergency stop command to the linear drive 31 of the drive unit 3 to urgently stop the imager 2.

The sensor 24 is a contact sensor configured to detect an obstacle by contact, or a proximity sensor (non-contact sensor) configured to detect an obstacle in a non-contact state, for example. From the viewpoint of avoiding contact between the imager 2 and an obstacle, the sensor 24 is preferably a proximity sensor. On the other hand, when the sensor 24 is a proximity sensor, the frequency of obstacle detection by the sensor 24 is likely to increase more than that when the sensor 24 is a contact sensor, and thus the frequency of emergency stop of the imager 2 tends to increase. Therefore, from the viewpoint of significantly reducing the frequency of emergency stop of the imager 2 and avoiding the complexity of the operation, the sensor 24 is preferably a contact sensor.

The sensor 24 includes two sensors, a first sensor 24a and a second sensor 24b. The first sensor 24a is a sensor 24 configured to detect an obstacle on a first side (X1 direction side in FIG. 1) in a direction of movement of the imager 2 by the linear drive 31 of the drive unit 3. The first sensor 24a is provided on a side face portion 23ba of the second portion 23b of the support 23 on the first side in the direction of movement of the imager 2 by the linear drive 31 of the drive unit 3. The second sensor 24b is a sensor 24 configured to detect an obstacle on a second side (X2 direction side in FIG. 1) in the direction of movement of the imager 2 by the linear drive 31 of the drive unit 3. The second sensor 24b is provided on a side face portion 23bb of the second portion 23b of the support 23 on the second side in the direction of movement of the imager 2 by the linear drive 31 of the drive unit 3.

The second portion 23b of the support 23 is provided with an operation panel 25 configured to allow an operator 300 (see FIGS. 1, 2A, and 2B) such as a technician to operate the X-ray imaging apparatus 100. The operation panel 25 is provided on a side face portion 23bc of the second portion 23b of the support 23 on the front side (Y1 direction side). As shown in FIG. 3, the operation panel 25 includes a plurality of operation buttons 25a and a handle 25b. The plurality of operation buttons 25a include operation buttons configured to allow the operator 300 to manipulate movement of the table 1, operation buttons configured to allow the operator 300 to input a setting value regarding X-ray irradiation, etc., for example. The handle 25b is a rod-like operation unit configured to allow the operator 300 to manipulate movement of the imager 2. When moving the imager 2 manually, the operator 300 moves the handle 25b in a direction in which the imager 2 is to be moved while holding the handle 25b.

The operation panel 25 also includes a permission button 25c (indicated by hatching) configured to allow the operator 300 to permit movement of the imager 2 using the sensor 24 described below. The permission button 25c is a push-button type switch. The permission button 25c includes a plurality of permission buttons. Specifically, the plurality of permission buttons 25c include two permission buttons, a first permission button 25ca and a second permission button 25cb. The first permission button 25ca is provided on the first side (X1 direction side in FIG. 1) in the direction of movement of the imager 2 by the linear drive 31 of the drive unit 3 in the operation panel 25 (side face portion 23bc). The second permission button 25cb is provided on the second side (X2 direction side in FIG. 1) in the direction of movement of the imager 2 by the linear drive 31 of the drive unit 3 in the operation panel 25 (side face portion 23bc).

(Structure Related to Movement of Imager at Emergency Stop)

Figure 4A:
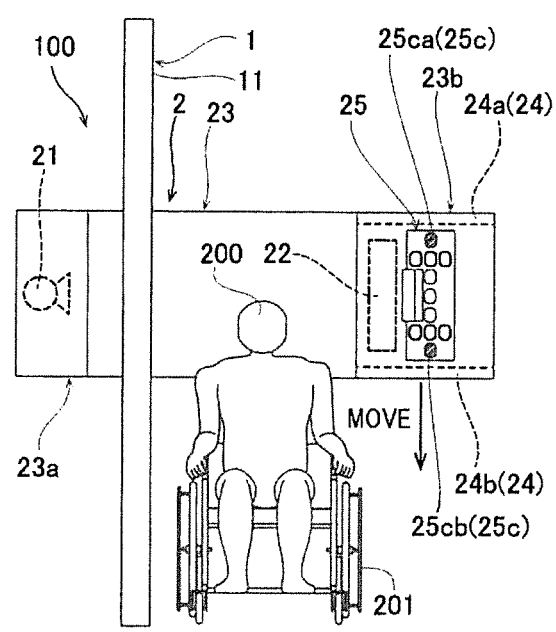
FIG. 4A is a schematic view illustrating movement of an imager by a drive unit.

As shown in FIGS. 4A and 4B, in the X-ray imaging apparatus 100, when an obstacle is detected in the traveling direction of the imager 2 by the sensor 24 while the imager 2 is moved by the linear drive 31 of the drive unit 3, movement of the imager 2 by the linear drive 31 of the drive unit 3 is urgently stopped. In this case, the operator 300 may want to move the imager 2 in an emergency stop state away from the obstacle by operating the handle 25b of the operation panel 25. However, during examination (imaging) of the subject 200 by the imager 2, the operator 300 may be on the back side of the imager 2 away from the handle 25b of the operation panel 25, as shown in FIGS. 1, 2A, and 2B, for example. In such a case, the hand of the operator 300 may not reach the handle 25b of the operation panel 25 sufficiently, and the operator 300 may not be able to satisfactorily operate the handle 25b.

Therefore, in this embodiment, as shown in FIG. 4C, the controller 6 is configured or programmed to control the linear drive 31 of the drive unit 3 to move the imager 2 in an emergency stop state in a direction opposite to the side on which the obstacle is detected by the sensor 24 when the operator 300 causes the sensor 24 to react while operating the permission button 25c in a state in which the imager 2 is urgently stopped due to the obstacle detected by the sensor 24. When it is desired to perform such control, the operator 300 can cause the sensor 24 to react with one hand while pressing the permission button 25c with the other hand, for example. A speed of movement of the imager 2 by the linear drive 31 of the drive unit 3 at this time is constant.

The controller 6 is configured or programmed to control the linear drive 31 of the drive unit 3 to move the imager 2 while the operator 300 causes the sensor 24 to react while operating the permission button 25c. That is, the controller 6 is configured or programmed to control the linear drive 31 of the drive unit 3 to stop the imager 2 when at least one of the operation of the permission button 25c and the reaction of the sensor 24 is not recognized.

In this embodiment, when the imager 2 in an emergency stop state is moved, any one of the two permission buttons 25ca and 25cb may be operated. Therefore, the operator 300 causes the sensor 24 to react while operating one of the two permission buttons 25ca and 25cb such that the controller 6 controls the linear drive 31 of the drive unit 3 to move the imager 2 in an emergency stop state in the direction opposite to the side on which the obstacle is detected by the sensor 24.

On the other hand, with regard to the sensor 24, it is necessary to cause one of the two sensors 24a and 24b that has detected the obstacle to react. Therefore, when the operator 300 causes the first sensor 24a to react while operating the permission button 25c in a state in which the imager 2 is urgently stopped due to the obstacle detected by the first sensor 24a, the controller 6 controls the linear drive 31 of the drive unit 3 to move the imager 2 in an emergency stop state in the direction opposite to the side on which the obstacle is detected by the first sensor 24a. Similarly, when the operator 300 causes the second sensor 24b to react while operating the permission button 25c in a state in which the imager 2 is urgently stopped due to the obstacle detected by the second sensor 24b, the controller 6 controls the linear drive 31 of the drive unit 3 to move the imager 2 in an emergency stop state in the direction opposite to the side on which the obstacle is detected by the second sensor 24b.

In examples shown in FIGS. 4A to 4C, the X-ray imaging apparatus 100 is in the second imaging state, and the subject 200 seated on the wheelchair 201 is an examination target (imaging target). In this case, first, as shown in FIG. 4A, the imager 2 is moved downward (Z2 direction) by the linear drive 31 of the drive unit 3 in order to image the subject 200. Then, as shown in FIG. 4B, the wheelchair 201 is detected as an obstacle by the first sensor 24a while the imager 2 is moved downward by the linear drive 31 of the drive unit 3. Consequently, downward movement of the imager 2 by the linear drive 31 of the drive unit 3 is urgently stopped. Thereafter, as shown in FIG. 4C, the operator 300 causes the first sensor 24a to react while operating the second permission button 25cb. Consequently, the imager 2 in an emergency stop state is moved upward (in a Z1 direction) by the linear drive 31 of the drive unit 3 away from the wheelchair 201 as an obstacle. At this time, the first permission button 25ca may be operated. Then, when the imager 2 is moved to a desired position, the operator 300 stops at least one of the operation of the second permission button 25cb and the reaction of the first sensor 24a. Thus, movement of the imager 2 by the linear drive 31 of the drive unit 3 is stopped. Thereafter, the operator 300 acts to remove the obstacle from the line of motion of the imager 2.

In FIGS. 4A to 4C, although the case in which the X-ray imaging apparatus 100 is in the second imaging state is described as an example for convenience of illustration, the aforementioned control is also applicable to the case in which the X-ray imaging apparatus 100 is in the first imaging state and the third imaging state.

Advantages of this Embodiment

According to this embodiment, the following advantages are obtained.

According to this embodiment, as described above, in the X-ray imaging apparatus 100, the drive unit 3 is configured to move the imager 2 in the direction opposite to the side on which an obstacle is detected by the sensor 24 when the operator 300 causes the sensor 24 to react while operating the permission button 25c. Accordingly, when the imager 2 is urgently stopped during examination of the subject 200, the operator 300 can move the imager 2 away from the obstacle using the permission button 25c and the sensor 24. Consequently, even when the operator 300 is at a position at which his or her hand cannot reach the handle 25b or at a position at which it is difficult for the operator 300 to hold the handle, the operator 300 can easily move the imager 2 away from the obstacle. Furthermore, as described above, the permission button 25c configured to allow the operator 300 to permit movement of the imager 2 using the sensor 24 is provided such that unlike the case in which the imager 2 is moved using only the sensor 24, the imager 2 cannot be moved unless the operator 300 intentionally operates the permission button 25c, and thus movement of the imager 2 without the intention of the operator 300 can be significantly reduced or prevented.

According to this embodiment, as described above, in the X-ray imaging apparatus 100, the drive unit 3 is configured to move the imager 2 while the operator 300 causes the sensor 24 to react while operating the permission button 25c. Accordingly, the operator 300 can stop movement of the imager 2 only by stopping the operation of the permission button 25c or the reaction of the sensor 24. Consequently, movement of the imager 2 can be stopped easily and quickly when it is desired to stop the movement of the imager 2.

According to this embodiment, as described above, the sensor 24 includes the first sensor 24a provided on the first side in the direction of movement of the imager 2 by the drive unit 3, and the second sensor 24b provided on the second side in the direction of movement of the imager 2 by the drive unit 3. Accordingly, both when the imager 2 moves to the first side in the direction of movement and when the imager 2 moves to the second side in the direction of movement, it is possible to detect an obstacle in the traveling direction of the imager 2 and urgently stop the imager 2.

According to this embodiment, as described above, in the X-ray imaging apparatus 100, the drive unit 3 is configured to move the imager 2 in an emergency stop state in the direction opposite to the side on which the obstacle is detected by the first sensor 24a when the operator 300 causes the first sensor 24a to react while operating the permission button 25c in a state in which the imager 2 is urgently stopped due to an obstacle detected by the first sensor 24a. Furthermore, in the X-ray imaging apparatus 100, the drive unit 3 is configured to move the imager 2 in an emergency stop state in the direction opposite to the side on which the obstacle is detected by the second sensor 24b when the operator 300 causes the second sensor 24b to react while operating the permission button 25c in a state in which the imager 2 is urgently stopped due to an obstacle detected by the second sensor 24b. Accordingly, both when the imager 2 is urgently stopped due to the obstacle detected by the first sensor 24a, and when the imager 2 is urgently stopped due to the obstacle detected by the second sensor 24b, the operator 300 can move the imager 2 away from the obstacle using the permission button 25c and the sensor 24.

According to this embodiment, as described above, the permission button 25c includes the plurality of permission buttons 25c. Furthermore, in the X-ray imaging apparatus 100, the drive unit 3 is configured to move the imager 2 in an emergency stop state in the direction opposite to the side on which an obstacle is detected by the sensor 24 when the operator 300 causes the sensor 24 to react while operating one of the plurality of permission buttons 25c. Accordingly, the operator 300 can move the imager 2 using the permission button 25c capable of being easily reached by his or her hand among the plurality of permission buttons 25c. Consequently, it is possible to more easily manipulate the movement of the imager 2 using the permission button 25c and the sensor 24.

According to this embodiment, as described above, the plurality of permission buttons 25c include the first permission button 25ca provided on the first side in the direction of movement of the imager 2 by the drive unit 3, and the second permission button 25cb provided on the second side in the direction of movement of the imager 2 by the drive unit 3. Accordingly, the first permission button 25ca and the second permission button 25cb are provided corresponding to the direction of movement of the imager 2 by the drive unit 3, and thus even when the imager 2 is moved to any position, it is possible to locate one of the first permission button 25ca and the second permission button 25cb at a position at which the hand of the operator 300 can easily reach the permission button 25c. Consequently, it is possible to still more easily manipulate the movement of the imager 2 using the permission button 25c and the sensor 24.

According to this embodiment, as described above, the permission button 25c is provided on the operation panel 25 provided with the operation buttons 25a other than the permission button 25c. Accordingly, the operation button 25c and the operation buttons 25a other than the permission button 25c can be collectively provided on the operation panel 25, and thus the complexity of the apparatus structure can be significantly reduced or prevented as compared with the case in which the permission button 25c is provided independently of the operation panel 25.

According to this embodiment, as described above, the sensor 24 is a contact sensor configured to detect an obstacle by contact or a proximity sensor configured to detect an obstacle in a non-contact state. When the sensor 24 is a contact sensor or a proximity sensor, an obstacle is detected at a position close to the imager 2, and thus the imager 2 is urgently stopped at a position close to the obstacle. Therefore, when the sensor 24 is a contact sensor or a proximity sensor, it is highly necessary to move the imager 2 in an emergency stop state away from the obstacle. Thus, when the sensor 24 is a contact sensor or a proximity sensor, with the aforementioned structure, the operator 300 can immediately move the imager 2 away from the obstacle using the permission button 25c and the sensor 24 even when the operator 300 is at the position at which his or her hand cannot reach the handle 25b or at the position at which it is difficult for the operator 300 to hold the handle in the configuration in which it is highly necessary to move the imager 2 in an emergency stop state away from the obstacle.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the X-ray imaging apparatus is an X-ray fluoroscopic imaging apparatus in the aforementioned embodiment, the present invention is not limited to this. According to the present invention, the X-ray imaging apparatus may alternatively be an X-ray imaging apparatus that cannot perform X-ray fluoroscopic imaging.

While the X-ray imaging apparatus is an under-tube type X-ray imaging apparatus in which an X-ray irradiator is provided below a table in the aforementioned embodiment, the present invention is not limited to this. According to the present invention, the X-ray imaging apparatus may alternatively be an overtube type X-ray imaging apparatus in which an X-ray irradiator is provided above a table.

While the X-ray imaging apparatus has the first imaging state, the second imaging state, and the third imaging state in the aforementioned embodiment, the present invention is not limited to this. According to the present invention, the X-ray imaging apparatus may not have all of the first imaging state, the second imaging state, and the third imaging state.

While the imager movable in the direction along the longitudinal direction of the table includes the X-ray irradiator and the X-ray detector in the aforementioned embodiment, the present invention is not limited to this. According to the present invention, the imager may alternatively be an X-ray irradiator movable in the direction along the longitudinal direction of the table, or an X-ray detector movable in the direction along the longitudinal direction of the table.

While the permission button includes the two permission buttons in the aforementioned embodiment, the present invention is not limited to this. According to the present invention, the permission button may alternatively be one permission button or may alternatively include three or more permission buttons.

While the plurality of permission buttons include the first permission button provided on the first side in the direction of movement of the imager by the drive unit and the second permission button provided on the second side in the direction of movement of the imager by the drive unit in the aforementioned embodiment, the present invention is not limited to this. According to the present invention, positions at which the plurality of permission buttons are provided may alternatively be any positions as long as it is easy for the operator to operate the plurality of permission buttons at the positions.

While the permission buttons are provided on the operation panel in the aforementioned embodiment, the present invention is not limited to this. According to the present invention, the permission buttons may alternatively be provided a portion other than the operation panel. For example, the permission buttons may alternatively be provided on any side face portion of the second portion of the support.

While in the X-ray imaging apparatus, the drive unit is configured to move the imager in an emergency stop state in the direction opposite to the side on which the obstacle is detected by the sensor when the operator causes the sensor to react while operating the permission button in a state in which the imager is urgently stopped due to the obstacle detected by the sensor in the aforementioned embodiment, the present invention is not limited to this. According to the present invention, in the X-ray imaging apparatus, the drive unit may alternatively be configured to move the imager in a state other than the emergency stop state in the direction opposite to the side on which the obstacle is detected by the sensor when the operator causes the sensor to react while operating the permission button in a state (a state in which the imager is simply stopped, for example) other than the state in which the imager is urgently stopped due to the obstacle detected by the sensor.

What is claimed is:

1. An X-ray imaging apparatus, comprising:
    a table on which a subject is placed;
    an imager configured to image the subject with X-rays;
    a drive unit configured to move the imager in a direction along a longitudinal direction of the table;
    a handle configured to allow an operator to manipulate movement of the imager;
    a sensor configured to detect an obstacle in a traveling direction of the imager when the imager is moved by the drive unit;
    a permission button configured to allow the operator to permit the movement of the imager using the sensor; and
    wherein the drive unit is configured to move the imager in a direction opposite to a side on which the obstacle is detected by the sensor when the operator causes the sensor to react while operating the permission button.

2. The X-ray imaging apparatus according to claim 1, wherein:
    the drive unit is configured to move the imager while the operator causes the sensor to react while operating the permission button.

3. The X-ray imaging apparatus according to claim 1, wherein:
    the sensor includes a first sensor provided on a first side in a direction of the movement of the imager by the drive unit, and a second sensor provided on a second side in the direction of the movement of the imager by the drive unit.

4. The X-ray imaging apparatus according to claim 3, wherein:
    the drive unit is configured to move the imager in an emergency stop state in a direction opposite to a side on which the obstacle is detected by the first sensor when the operator causes the first sensor to react while operating the permission button in a state in which the imager is urgently stopped due to the obstacle detected by the first sensor; and
    the drive unit is configured to move the imager in the emergency stop state in a direction opposite to a side on which the obstacle is detected by the second sensor when the operator causes the second sensor to react while operating the permission button in a state in which the imager is urgently stopped due to the obstacle detected by the second sensor.

5. The X-ray imaging apparatus according to claim 1, wherein:
    the permission button includes a plurality of permission buttons; and
    the drive unit is configured to move the imager in an emergency stop state in the direction opposite to the side on which the obstacle is detected by the sensor when the operator causes the sensor to react while operating one of the plurality of permission buttons.

6. The X-ray imaging apparatus according to claim 5, wherein:
    the plurality of permission buttons include a first permission button provided on a first side in a direction of the movement of the imager by the drive unit, and a second permission button provided on a second side in the direction of the movement of the imager by the drive unit.

7. The X-ray imaging apparatus according to claim 1, wherein:
    the permission button is provided on an operation panel provided with an operation button other than the permission button.

8. The X-ray imaging apparatus according to claim 1, wherein:
    the sensor is a contact sensor configured to detect the obstacle by contact or a proximity sensor configured to detect the obstacle in a non-contact state.

* * * * *